(12) United States Patent
Rupieper et al.

(10) Patent No.: US 6,581,440 B1
(45) Date of Patent: Jun. 24, 2003

(54) PROCESS AND DEVICE FOR DETERMINING CHANGES IN LIQUID MEDIA, IN PARTICULAR COATING AGENTS UNDER SHEAR STRESS

(75) Inventors: Paul Rupieper, Wuppertal (DE); Michael Höffer, Wuppertal (DE); Christian Voyé, Gevelsberg (DE)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/723,510

(22) Filed: Nov. 28, 2000

(30) Foreign Application Priority Data

Dec. 4, 1999 (DE) .......................... 199 58 489

(51) Int. Cl.⁷ .............................................. G01N 11/04
(52) U.S. Cl. ...................... 73/54.11; 73/54.04; 73/54.39
(58) Field of Search ........................... 73/54.04, 54.11, 73/54.39, 64.56, 815

(56) References Cited

U.S. PATENT DOCUMENTS

| | | | | |
|---|---|---|---|---|
| 2,781,662 A | * | 2/1957 | Brewer .................. 73/54.11 |
| 3,473,368 A | * | 10/1969 | Roper ..................... 73/152.04 |
| 3,911,728 A | * | 10/1975 | Fixot ........................ 73/54.04 |
| 3,928,707 A | * | 12/1975 | Lauterbach et al. ..... 106/217.3 |
| 5,172,585 A |   | 12/1992 | Gleissle |
| 5,257,528 A | * | 11/1993 | Degouy et al. ............ 73/53.01 |
| 5,447,440 A | * | 9/1995 | Davis et al. .................. 422/73 |
| 5,900,539 A | * | 5/1999 | Tremblay et al. .......... 73/54.11 |
| 5,987,969 A | * | 11/1999 | Joseph et al. .............. 73/53.01 |
| 6,098,450 A | * | 8/2000 | Willenbacher et al. .... 73/54.01 |

FOREIGN PATENT DOCUMENTS

| | | |
|---|---|---|
| DE | 3919828 | 12/1990 |
| DE | 19848687 | 4/2000 |
| EP | 0102435 B1 | 3/1984 |
| EP | 0391331 B1 | 10/1990 |
| EP | 0595276 A3 | 5/1994 |

\* cited by examiner

Primary Examiner—Hezron Williams
Assistant Examiner—Michael Cygan
(74) Attorney, Agent, or Firm—Bart E. Lerman

(57) ABSTRACT

A process and a device for determining changes in a liquid medium, in particular a liquid coating agent or its components, caused by shear stress, in which a given volume of the medium is allowed to pass repeatedly through a shear unit under reproducible conditions.

3 Claims, 1 Drawing Sheet

Figure 1:
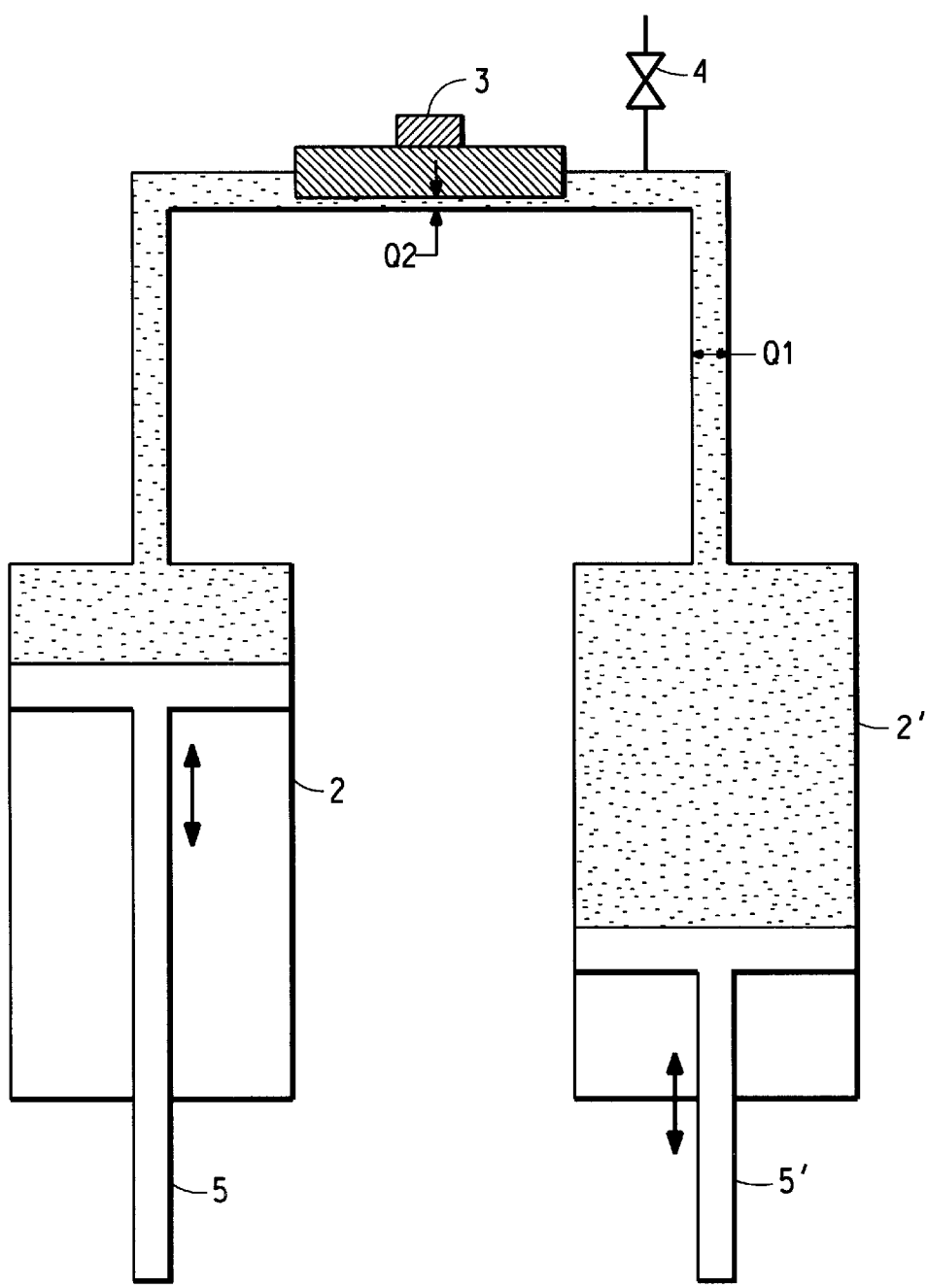

PROCESS AND DEVICE FOR DETERMINING CHANGES IN LIQUID MEDIA, IN PARTICULAR COATING AGENTS UNDER SHEAR STRESS

BACKGROUND OF THE INVENTION

The present invention provides a process for investigating and determining changes in liquid media, in particular coating agents and their components, due to shear stress and also a device for performing the process.

Liquid media which contain disperse constituents may experience irreversible changes or damage when they are subjected to shear stress.

Typical examples of liquid media which contain disperse constituents being subjected to shear stress can be the liquid lacquers passed through circular pipework systems for the purpose of supplying the spraying devices during mass production lacquering. The liquid lacquers are pumped from a storage tank into the circular pipework, some is removed via the spraying devices during the application of lacquer and the unused remainder is then returned to the storage tank and mixed with the lacquer material found therein. Whereas the liquid lacquer in the storage tank is under atmospheric pressure, it is under a pressure of, for example, up to 12 bar in the circular pipework. The liquid lacquer being circulated experiences pressure differences within the circular pipework which are produced, for example, upstream and downstream, with respect to the direction of flow, of components installed in the circular pipework, in particular for example upstream and downstream of pumps and valves. The shear stress then acting on the liquid lacquer can lead to damage of disperse binder constituents and/or pigments. The extent of damage may be such that the liquid lacquer can no longer be used. The damage may consist, for example, of an unwanted and irreversible change in the Theological behaviour, the production of specks in the lacquer and/or changes in the final finishing effect or colour. The stability to shear of a given liquid lacquer is not known exactly. In practice, testing for these types of changes takes place empirically, for example by taking a sample and using conventional application-oriented tests. The liquid lacquer samples taken have not been subjected to defined, reproducible shear stress.

In order to test the stability to shear or stability to circular pipework of liquid lacquers, it has been disclosed that a quantity of the liquid lacquer to be tested be stirred magnetically and tested for changes in the lacquer material by taking samples after a defined period. This method correlates with the shear stresses in a circular pipework installation to only a limited extent and suffers in particular from very poor reproducibility.

BRIEF SUMMARY OF THE INVENTION

The object of the invention is the provision of a reproducible method for testing the effects of shear stresses on liquid media, in particular liquid coating agents.

The object is achieved by repeatedly subjecting a given volume of a liquid medium to shear under defined conditions.

Thus, the invention provides a process for determining reversible or irreversible changes in a liquid medium during the exertion of a shear stress which is characterised in that a given volume of the liquid medium to be tested is allowed to pass repeatedly through a shear unit under reproducible conditions.

DETAILED DESCRIPTION OF THE INVENTION

In the process according to the invention, a given volume, for example 500 to 2000 ml, of a liquid medium to be subjected to a shear stress is allowed to pass repeatedly through a shear unit under defined conditions. In general, the shear stress is applied at temperatures of, for example, 20 to 50° C. It is expedient that as much as possible of the given volume of liquid medium is allowed to pass through the shear unit during each passage through the shear unit. The proportion of non-sheared material per passage through the shear unit is preferably less than 5%, in particular less than 1%.

The liquid medium passes repeatedly through the shear unit, i.e. a predetermined number of, for example, 50 to 2000 passes, and experiences a shear gradient of, for example, between 100 and $10^7 s^{-1}$ when passing through the shear unit. The shear stress in the liquid medium is produced as a result of the prevailing shear gradient and the number of repeated passages through the shear unit. The shear gradient itself is produced in the given liquid medium by the pressure difference P2-P1 prevailing upstream and downstream, with respect to the direction of flow, of the shear unit. Immediately upstream of the shear unit the liquid medium builds up under the initial pressure P1 of, for example, 5 to 50 bar, and the rate of flow is low, during passage through the shear element the rate of flow is high, on leaving the shear unit the pressure in the liquid medium is reduced to the pressure P2<P1 and the rate of flow is again low. P2 generally corresponds to ambient atmospheric pressure, or slightly higher than that. For a given liquid medium, a given temperature and a given pressure P2 in the liquid medium, the size of the shear gradient depends on the initial pressure P1 upstream of the shear unit and on the cross-section of the shear unit. It is obvious to a person skilled in the art that, in the case of a non-ideal circular cross-section in the shear unit, there is an additional effect on P1 and thus on the shear gradient.

A constriction in the cross-section, within a closed deaerated pipe system which contains a given volume of the liquid medium, is used as the shear unit. The deaerated status ensures that the liquid medium is present as an incompressible or virtually incompressible liquid. The pipe system itself has a cross-section which does not produce a significant shear effect on the liquid medium. The constriction in the cross-section being used as the shear unit, however, is of such a size that the liquid medium is subjected to shear while passing through the shear unit. For example, the cross-section in the pipe system is greater than 10 mm$^2$, for example 10 to 10000 mm$^2$, whereas the cross-section in the shear unit is, for example, 0.5 to 10 mm$^2$, preferably less than 5 mm$^2$. The constriction in the cross-section my have a fixed value, but it is preferably an adjustable constriction in the cross-section so that, for example, the shear gradient in a liquid medium subjected to a given initial pressure P1 can be adjusted to a desired value. The shear unit may expediently be a gap which can be adjusted by means of a micrometer screw, for example to a gap width of 0.1 to 3 mm.

The pipe system may be designed as a closed circuit for the liquid medium. A single complete circuit executed therein by the entire volume of the liquid medium then corresponds to a single passage through the shear unit. The pipe system is preferably one in which the given volume of liquid medium can pass as completely as possible through the shear unit in a shuttle process with repeated changes in the direction of flow. In the process according to the invention, liquid media are subjected to a defined and reproducible shear stress, in particular in order to test their stability under shear stress. For example, it can be tested whether a change in or damage to a liquid medium occurs under shear stress, whether a change or damage occurring under shear stress is reversible or irreversible, how rapidly, i.e. after how many passages through the shear unit, a change or damage occurs in the liquid medium or how great is the extent of a change in or damage to the liquid medium after a predetermined amount of shear stress, i.e. after a predetermined number of passages through the shear unit. The process according to the invention enables the provision of correct answers to these questions. Finally, the entire volume, or at least approximately the entire volume, of the liquid medium is subjected to uniform shear stress during each individual passage through the shear unit; thus the shear stress as such is exerted in a defined and reproducible way.

In order to ensure the presence of a defined and reproducible shear stress, the shear gradient can be kept constant during one shear cycle consisting of a defined number of passages through the shear unit, and this is also preferred. For this purpose, it may be necessary, for example, to compensate for a possible change in temperature or a change in the initial pressure $P1$ being produced as a result of a change in the liquid medium during the application of shear stress. For example, it may be necessary to thermostat the liquid medium or to adapt the initial pressure $P1$ to altered rheological behaviour of the liquid medium resulting from the shear stress, and thus to keep the shear gradient constant. The initial pressure $P1$ can be controlled by changing the constriction in the cross-section in the shear unit and/or by altering the force acting on the liquid medium upstream, with respect to the direction of flow, of the shear unit.

In a second embodiment of the process according to the invention a shear gradient which changes during one shear cycle due to a change in the material can also be used, by not taking any of the compensatory measures explained above. In this case, a defined and reproducible shear stress in the liquid medium is also ensured.

In a third embodiment of the process according to the invention, one parameter only is deliberately varied during a shear cycle, while the other parameters are kept constant. Examples of variable parameters are the initial pressure $P1$, the cross-section of the shear unit and the temperature of the liquid medium.

The liquid media being subjected to shear stress in the process according to the invention are, for example, multi-phase systems in the sense of liquid media which contain disperse liquid or solid constituents. In particular they are liquid coating agents which contain disperse constituents such as pigments, fillers and/or disperse binders. They may be pigment-containing or pigment-free liquid coating agents. The liquid coating agents may be solvent-free, solvent-containing or aqueous. They may be single component lacquers or else the individual components of multi-component lacquers. They may be physically drying or chemically cross-linking liquid coating agents. In the context of the present invention, the expression "coating agents" also includes liquid binders and semi-finished products which are suitable for preparing liquid coating agents. Examples are binders which are present in the disperse form or which contain disperse constituents, for example aqueous or non-aqueous binder dispersions or emulsions. Examples of liquid coating agents in a narrower sense are liquid clear lacquers, colour-providing or effect-providing base lacquers, topcoat lacquers, pigment pastes and filler lacquers.

In all embodiments, the present invention also provides a process for determining reversible or irreversible changes due to shear stress in a liquid medium which is characterised in that a given volume of the liquid medium is allowed to pass repeatedly through a shear unit under defined conditions, wherein the liquid medium is tested for changes in the material during and/or after completion of the shear cycle consisting of repeated passages through the shear unit.

During and/or after finishing a shear cycle, the shear-stressed liquid medium can be tested for reversible or irreversible changes or damage which has occurred due to the shear stress. For this purpose, a sample of the liquid medium, for example 10 to 300 ml, may be taken once or several times within a shear cycle consisting of a number of passages or the total amount of liquid medium available may be used for testing. A sample may be taken at any time, but is preferably taken only after completion of an individual passage by the liquid medium found in the pipe system through the shear unit. It is advantageous that sample-taking during a shear cycle has no effect at all on the defined shear stress in the liquid medium and the reproducibility of the process according to the invention.

Testing the samples taken may comprise tests or measurements which can be performed directly with the liquid medium or indirect tests of the liquid medium, for example application-oriented tests on function or usability. Example of tests or measurements which can be performed directly with the liquid medium, in particular liquid coating agent, are viscosity measurements, measuring the resonance frequency of the liquid material using a viscosity measurement instrument, visual assessment, tests on speck production, tests on settling behaviour, optical measurements on the liquid lacquer, for example liquid lacquer colorimetry. Examples of indirect tests on the liquid media, in particular on liquid coating agents, are testing the processability and tests on coating layers obtained by applying the liquid coating agent and then optionally drying or curing for example determining the sagging limit, micoscopic tests on the films obtained, colorimetry, brightness and gloss measurements, visual assessment and drawing up property/layer thickness correlation diagrams in accordance with the procedure described in EP-B 0 842 414.

Testing the shear-stressed liquid medium may optionally also be performed on the liquid medium found inside the pipe system, with the liquid medium either stationary or flowing. Tests on the liquid medium found inside the pipe system comprise measurements performed directly in the liquid medium, for example in-line temperature measurement upstream and downstream of the shear unit, in-line measurement of the initial pressure $P1$ and/or the pressure $P2$, in particular also in-line measurement of theological data or the resonance frequency of the liquid medium using a measuring unit with a vibration transmitter (resonator). The actual values obtained by in-line measurements can be used in particular to control the compensatory measures mentioned during the explanation of the first embodiment of the process according to the invention for exerting a shear stress.

Measurement of the force required to produce the pressure $P1$ acting on the liquid medium or determination of the rate of flow of the liquid medium may be used for indirect determination of the condition of or a change in the shear-stressed liquid medium. The rate of flow of the liquid medium may be determined, for example, indirectly by a pathlength/time measurement in the metering system, given that the cross-section of the metering system is known.

The measured values being produced, in particular as a set of measurements, may be stored and evaluated, for example using a computer (PC).

The tests performed in-line or on samples taken from the liquid medium are used to determine the condition, or rather the change in condition, during or after defined shear stress. For example, a change in condition, e.g. the degree of change or damage, may be determined and plotted as a function of increasing shear stress. The change of measured values with increasing shear stress within the context of one shear cycle may, for example, enable conclusions to be made about the type of change in or damage to the liquid medium. If the shear-stressed liquid medium is a liquid coating agent, for example, a relationship may be produced with the shear stress prevailing within a circular pipe system.

The test results may be used, for example, to characterise the condition of a given liquid medium, for example a liquid coating agent, before, during and after defined shear stress.

The process according to the invention for exerting shear stress and for subsequent or accompanying determination of the ability to apply shear stress to a liquid coating agent can be used for example, in the field of pigment, lacquer and binder development. It can also be used in quality control, for example during batch testing in the production of lacquers or during goods acceptance checks.

The process according to the invention can be used for determining setpoint values for the ability to apply shear stress to liquid media such as, for example, liquid coating agents.

The invention also provides a device for performing the process according to the invention in a closed, deaerated pipe system which contains the given volume of liquid medium and which contains a shear unit for the liquid medium. The pipe system is arranged so that the liquid medium is subjected to shear stress substantially only in the shear unit when performing the process according to the invention, i.e. the inner surface of the pipe system per se, including the inner surface of the shear unit, is smooth and has no ridges. The shear unit is, for example, a constriction in the cross-section of the pipe system, for example in the form of a gap. The shear unit is preferably one with an adjustable cross-section, for example a gap which can be adjusted using a micrometer screw.

One embodiment of the device according to the invention is a pipe system designed as a closed circuit for the liquid medium which includes a pump for the liquid medium and a shear unit. One complete circuit of the entire volume of the liquid medium in the pipe system laid out in this way corresponds to one passage through the shear unit.

A preferred embodiment of the device according to the invention is a pipe system which consists of two cylinders with pistons which are linked to each other via piping containing a shear unit for the liquid medium. This expediently contains two cylinders with the same internal capacity. Each of the cylinders may be emptied completely by means of a plunger which is driven, for example, pneumatically. At the start of a shear cycle, the deaerated pipe system is filled with a given volume of the liquid medium, the piston in one cylinder is pushed fully in while the other, in accordance with the amount of liquid involved, is pushed out. The given volume of liquid medium can now be pushed from one cylinder into the other in an alternating procedure with repeated changes in the direction of flow. In order to ensure as complete passage as possible through the shear unit each time, the connection pipe linking the two cylinders and containing the shear unit has a dead space with only a small capacity, for example less than 5%, preferably less than 1% of the given volume of coating agent. The dead space can be kept to a small value, for example, by choosing short connection pipes with a relatively small cross-section, but one which does not cause any shear.

Conventional measuring instruments may be incorporated for in-line pressure and in-line temperature measurements. For measuring theological data or the resonance frequency of the liquid medium, a measuring unit with a vibration transmitter (resonator), in particular for instance a piezoelement, may be incorporated, expediently in a module with the shear unit.

BRIEF DESCRIPTION OF THE DRAWING

FIG. 1 is a schematic cross-sectional representation of an example of the preferred embodiment of the device according to the invention which is suitable for performing the process according to the invention. This consists of two cylinders (2, 2') with pistons (5, 5'), connected via a connection pipe (1) with a cross-section Q1. The connecting pipe contains a shear unit (3) with an adjustable cross-section Q2<Q1. A valve (4) for sample-taking is also shown. The device is deaerated and filled with a liquid medium (6) to be tested, e.g. a lacquer. The total volume of this can be pushed from one cylinder into the other in an alternating procedure with repeated changes in the direction of flow.

Using the process according to the invention and the device according to the invention, liquid media, in particular liquid coating agents, can be subjected to shear stress in a defined and reproducible manner and reversible or irreversible changes of the liquid medium can be determined. The process according to the invention is reproducible; it can be performed in an automated manner. Depending on the particular embodiment of the process according to the invention, the effects of shear stress in the shear-stressed liquid medium can be tested without taking a sample of the liquid or after taking a sample of the liquid.

What is claimed is:

1. A device for determining changes in a liquid medium, wherein a given volume of the liquid medium to be tested is allowed to pass repeatedly through a shear unit under defined, reproducible and uniform shear stress conditions, said device comprising a closed, deaerated pipe system suitable for accepting a given volume of a liquid medium with a shear unit for the liquid medium and structure for repeating passage of the given volume of liquid medium through the shear unit; wherein the device consists of a first cylinder and a second cylinder each cylinder containing a piston disposed within the cylinder, said cylinders being connected to each other via a connecting pipe and wherein the connecting pipe contains the shear unit and whereby liquid medium is repeatedly forced by the piston from the first cylinder through the shear unit into the second cylinder and then forced by the piston of the second cylinder back through the shear unit and into the first cylinder.

2. The device of claim 1 wherein the device has a means for taking samples of liquid medium contained in the device.

3. The device of claim 1 wherein the liquid medium is a coating agent.

* * * * *

UNITED STATES PATENT AND TRADEMARK OFFICE
CERTIFICATE OF CORRECTION

PATENT NO. : 6,581,440 B1
DATED : June 24, 2003
INVENTOR(S) : Paul Rupieper, Michael Hoffer and Christian Voye It is certified that error appears in the above-identified patent and that said Letters Patent is hereby corrected as shown below:

Column 1,
Line 37, the word "Theological" should read -- rheological --.

Column 4,
Line 49, the word "theological" should read -- rheological --.

Column 6,
Line 9, the word "theological" should read -- rheological --.

Signed and Sealed this

Twenty-eighth Day of October, 2003

JAMES E. ROGAN
*Director of the United States Patent and Trademark Office*